(12) United States Patent
Ryu et al.

(10) Patent No.: US 11,028,046 B2
(45) Date of Patent: Jun. 8, 2021

(54) TOLUENE DIISOCYANATE PURIFICATION METHOD

(71) Applicant: HANWHA CHEMICAL CORPORATION, Seoul (KR)

(72) Inventors: Hyun Cheol Ryu, Daejeon (KR); Kee Do Han, Daejeon (KR); Seong Ho Park, Daejeon (KR); Chang Mo Chung, Daejeon (KR)

(73) Assignee: HANWHA CHEMICAL CORPORATION, Seoul (KR)

( * ) Notice: Subject to any disclaimer, the term of this patent is extended or adjusted under 35 U.S.C. 154(b) by 49 days.

(21) Appl. No.: 16/463,972

(22) PCT Filed: Dec. 12, 2017

(86) PCT No.: PCT/KR2017/014566
§ 371 (c)(1),
(2) Date: May 24, 2019

(87) PCT Pub. No.: WO2018/110947
PCT Pub. Date: Jun. 21, 2018

(65) Prior Publication Data
US 2020/0377447 A1    Dec. 3, 2020

(30) Foreign Application Priority Data

Dec. 15, 2016   (KR) .......................... 10-2016-0171843
Dec. 11, 2017   (KR) .......................... 10-2017-0169654

(51) Int. Cl.
*C07C 263/20*        (2006.01)
*B01D 3/00*          (2006.01)
(Continued)

(52) U.S. Cl.
CPC ............ *C07C 263/20* (2013.01); *B01D 3/009* (2013.01); *B01D 3/141* (2013.01); *B01D 3/322* (2013.01); *B01D 5/006* (2013.01)

(58) Field of Classification Search
None
See application file for complete search history.

(56) References Cited

U.S. PATENT DOCUMENTS 7,108,770 B2    9/2006    Grün et al.
7,118,653 B2    10/2006   Brady et al.
(Continued)

FOREIGN PATENT DOCUMENTS

CN    1467202    1/2004
CN    1496978    5/2004
(Continued)

OTHER PUBLICATIONS

WIPO, PCT Search Report & Written Opinion of PCT/KR2017/014566 dated Mar. 22, 2018.
(Continued)

*Primary Examiner* — Amy C Bonaparte
(74) *Attorney, Agent, or Firm* — Lex IP Meister, PLLC

(57) ABSTRACT

The present invention relates to a toluene diisocyanate purification method enabling acquisition of a product having a small amount of dimers in a final product by means of using a reactive dividing wall column during toluene diisocyanate preparation. More particularly, according to the present invention, in order to obtain a product having a small amount of dimers in accordance with a reversible reaction of a monomer and a dimer, a purification procedure is designed by means of applying the temperature, pressure, time of stay and the like of a reactive dividing wall column as appropriate particular conditions, a reboiler having short time of stay and high heat transfer rate is used, and thus a dimerization
(Continued)

reaction is inhibited and the purity and yield of the product are enhanced. Therefore, high-purity toluene diisocyanate can be purified and obtained.

13 Claims, 2 Drawing Sheets

(51) Int. Cl.
　　　*B01D 3/14*　　　(2006.01)
　　　*B01D 3/32*　　　(2006.01)
　　　*B01D 5/00*　　　(2006.01)

(56) References Cited

U.S. PATENT DOCUMENTS

| | | |
|---|---|---|
| 7,358,388 B2 | 4/2008 | Woelfert et al. |
| 2003/0230476 A1 | 12/2003 | Brady et al. |
| 2004/0118672 A1 | 6/2004 | Grun et al. |
| 2006/0135810 A1 | 6/2006 | Wolfert et al. |
| 2007/0015934 A1 | 1/2007 | Wolfert et al. |
| 2007/0287857 A1 | 12/2007 | Zechlin et al. |
| 2010/0249450 A1 | 9/2010 | Maeba et al. |
| 2011/0172458 A1 | 7/2011 | Merenov et al. |
| 2011/0178328 A1 | 7/2011 | Merenov et al. |

FOREIGN PATENT DOCUMENTS

| | | |
|---|---|---|
| CN | 1729165 | 2/2006 |
| CN | 1802344 | 7/2006 |
| CN | 101774949 | 7/2010 |
| CN | 101827812 | 9/2010 |
| CN | 102224132 | 10/2011 |
| CN | 102224133 | 10/2011 |
| EP | 1371635 | 12/2003 |
| JP | 2004-143173 | 5/2004 |
| JP | 2004-155760 | 6/2004 |
| JP | 2006-510696 | 3/2006 |
| JP | 2009-120528 | 6/2009 |
| JP | 2012-504643 | 2/2012 |
| JP | 2012-504644 | 2/2012 |
| KR | 10-2003-0096037 | 12/2003 |
| KR | 10-2004-0035567 | 4/2004 |
| KR | 10-2004-0105883 | 12/2004 |
| KR | 10-2010-0101088 | 9/2010 |
| KR | 10-0984426 | 9/2010 |
| KR | 10-0984460 | 9/2010 |
| KR | 10-1020373 | 3/2011 |

OTHER PUBLICATIONS

Schultz M A et al, "Reduce Costs with Dividing-Wall Columns", Chemical Engineering Progress, American Institute of Chemical Engineers, NY, US, p. 64-71, May 1, 2002, XP001106017.
EPO, Supplementary European Search Report of EP 17881662.5 dated Jul. 9, 2020.

TOLUENE DIISOCYANATE PURIFICATION METHOD

TECHNICAL FIELD

Cross-Reference to Related Applications

This application claims priority to and the benefit of Korean Patent Application No. 10-2016-0171843 filed in the Korean Intellectual Property Office on Dec. 15, 2016, and Korean Patent Application No. 10-201 7-0169654 filed in the Korean Intellectual Property Office on Dec. 11, 2017, the entire contents of which are incorporated herein by reference.

The present invention relates to a toluene diisocyanate purification method capable of obtaining a purified product with high purity through inhibition of a dimerization reaction by using a reactive dividing wall column to specify operating conditions of the column for a reaction mixture obtained during toluene diisocyanate preparation.

BACKGROUND ART

Toluene diisocyanate is used as a precursor for producing polyurethane which is a raw material of cloth, fiber, paint, and the like. With an increase in an amount of polyurethane used, an amount of toluene diisocyanate used as a raw material is also gradually increasing.

Toluene diisocyanate is prepared by reacting phosgene and toluene diamine in a solvent such as toluene, monochlorobenzene, or the like. The prepared reaction mixture contains not only a product but also unreacted material, solvent, low-boiling components, and high-boiling components, and thus toluene diisocyanate is purified from the reaction mixture through a series of purification processes and used.

For example, Korean Patent No. 10-1020373 and Korean Patent No. 10-0984426 disclose a method of using a bulkhead column for final purification of a toluene diisocyanate (TDI) product in a TDI distillation method. In addition, Korean Patent No. 10-0984460 discloses a TDI distillation method using a heat integration system.

However, these methods have focused only on maximizing energy efficiency by primarily applying a dividing wall column to separate low-boiling components, that is, unreacted (phosgene) and solvent/product (toluene diisocyanate)/high-boiling components. Further, these methods have a problem of not considering generation and removal of impurities by a dimerization reaction of toluene diisocyanate present in the reaction mixture.

DISCLOSURE

Technical Problem

The present invention relates to a process subsequent to separation of unreacted materials and a solvent in advance. The present invention has been made in an effort to provide a toluene diisocyanate purification method having advantages of obtaining a high-purity toluene diisocyanate by reflecting an inhibition of a dimerization reaction in toluene diisocyanate obtained by purification of the solvent and unreacted materials in advance after preparation of toluene diisocyanate.

Technical Solution

An exemplary embodiment of the present invention provides a toluene diisocyanate purification method including: separating and purifying toluene diisocyanate by feeding a mixture containing toluene diisocyanate as a main component to a reactive dividing wall column equipped with a condenser and a reboiler, wherein a pressure of the condenser is maintained at 50 torr or less, and a temperature of the condenser is maintained at 130° C. or less, a total pressure difference in the reactive dividing wall column is maintained at 40 torr or less, and a retention time of the reaction mixture in the reactive dividing wall column is maintained within 10 seconds to 150 seconds.

Advantageous Effects

The present invention is effective to provide the toluene diisocyanate purification method capable of greatly inhibiting the dimerization reaction of the reaction mixture obtained in the preparation of toluene diisocyanate to enhance the product quality by using a reactive dividing wall column equipped with a reboiler and a condenser at a low pressure and a low temperature as compared to the conventional method and controlling operating conditions. Further, in the present invention, the product quality may be maintained by further quenching in order to prevent a reversible reaction which is generated after purification of toluene diisocyanate. Therefore, the present invention may effectively obtain high-purity toluene diisocyanate in which thermal denaturation is minimized.

MODE FOR INVENTION

Figure 1:
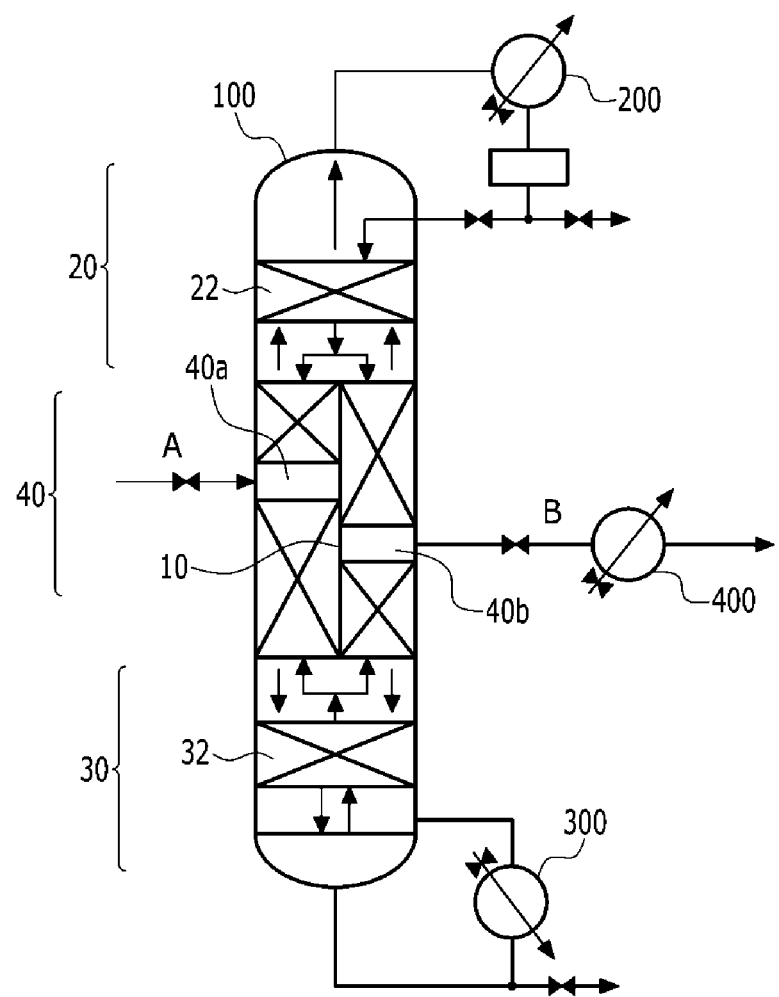
FIG. 1 shows a reactive dividing wall column according to an embodiment of the present invention.

In the present invention, terms such as first, second, and the like, are used to describe various components, and these terms are used only for the purpose of distinguishing one component from another.

In addition, terms used herein are used for the purpose of describing exemplary embodiments only and are not intended to limit the present invention. The singular expressions include a plurality of expressions unless expressly stated otherwise in the context. Terms used herein such as "comprise", "include", "have", and the like, should be understand to indicate that there are practiced features, numbers, steps, components, or combinations thereof, and not to exclude the possibility of presence or addition of one or more other features, numbers, steps, components, or combinations thereof in advance.

Further, in the present invention, formation of each layer or element "on" or "above" each layer or element means that each layer or element is directly formed above each layer or element, or other layers or elements may be additionally formed between each layer, or on an object, or on a substrate.

The present invention may be variously modified and may have various forms, and thus specific embodiments are illustrated and described in detail below. However, the present invention is not limited to the specific embodiments and should be construed as including all the changes, equivalents, and substitutions included in the spirit and scope of the present invention.

Hereinafter, the present invention is described in detail.

According to an embodiment of the present invention, there is provided a toluene diisocyanate purification method including: separating and purifying toluene diisocyanate by feeding a mixture containing toluene diisocyanate as a main component to a reactive dividing wall column equipped with a condenser and a reboiler, wherein a pressure of the condenser is maintained at 50 torr or less, and a temperature of the condenser is maintained at 130° C. or less, a total pressure difference in the reactive dividing wall column is maintained at 40 torr or less, and a retention time of the reaction mixture in the reactive dividing wall column is maintained within 10 seconds to 150 seconds. The present invention relates to the toluene diisocyanate purification method with high efficiency capable of obtaining a purified product with high purity through inhibition of a dimerization reaction by using a reactive dividing wall column, using a reboiler having short time of stay and high heat transfer rate such as a falling film evaporator, and using a condenser quenching a final product for the reaction mixture obtained in preparation of toluene diisocyanate. Thus, the present invention may improve the purity and yield of the product through inhibition of the dimerization reaction.

Specifically, the present invention provides the toluene diisocyanate purification method with high purity by reflecting the inhibition of the dimerization reaction in toluene diisocyanate obtained by purification of the solvent and unreacted materials in advance.

In particular, the present inventors confirmed the presence of dimerization reaction of toluene diisocyanate in the column according to the temperature and the retention time, and developed a method of specifying operating conditions of the column to inhibit the dimerization reaction.

The method according to the present invention may be performed using the reactive dividing wall column having at least one condenser and reboiler. The reactive dividing wall column is fed with the mixture containing toluene diisocyanate as a main component, and toluene diisocyanate is separated and purified by controlling the pressure and temperature of the column and the retention time of the mixture.

The exact name of the column applied in the present invention is specifically a reactive dividing wall column, which includes the reaction. A part of the reaction is not mentioned in conventional documents. In addition, the method of the present invention is different from conventional general separation processes since the method of the present invention deals with a process subsequent to separation of a solvent, a unreacted phosgene, and the like, in advance.

Thus, the reactive dividing wall column used in the present invention may be an apparatus for separating a low-boiling component and a high-boiling component at a time from a mixture in which the unreacted materials and solvent are removed in advance and increasing the purity of the product.

In addition, in the reactive dividing wall column, a space divided by a dividing wall of a main column serves as a pre-separator, and thus the high-boiling component and the low-boiling component may be separated and purity of a desired product may be improved. Further, in the present invention, the dimerization reaction of the product may be inhibited by appropriately controlling not only the temperature and the pressure of the condenser in this apparatus but also the retention time in the main column.

In addition, in the specification of the present invention, the "mixture containing toluene diisocyanate as a main component" which is a purification subject may be a mixture mainly including toluene diisocyanate by separating unreacted materials and solvent from the reaction product generated in general preparation of toluene diisocyanate. For example, the mixture containing toluene diisocyanate as a main component is a mixture including toluene diisocyanate, a toluene diisocyanate dimer, a low-boiling component, and a high-boiling component recovered by separating unreacted materials and a solvent from a mixture in which phosgene and toluenediamine are reacted in the solvent. Further, the term "main component" in the specification of the present invention means a component that accounts for about 70 wt % or more, or about 80 wt % or more, or about 85 wt % or more based on a total weight of the mixture or composition containing the main component.

Further, the low-boiling component means low-boiling impurities generated in preparation of toluene diisocyanate, and may include chlorine-containing impurities directly or indirectly caused from well-known phosgene. The high-boiling component may include high-boiling impurities such as polymerizable isocyanate, a hydrolyzable chloride compound, and the like.

In addition, in the following description of the reactive dividing wall column, component separated and discharged to an upper part of the dividing wall may be classified as the low-boiling components, components separated and discharged to a lower part of the dividing wall may be classified as high-boiling components, and component separated and discharged to an side draw zone of the main column may be classified as products.

Meanwhile, toluene diisocyanate generates a reversible reaction in which two monomer units of toluene diisocyanate are combined to form a dimer, and the dimer is decomposed into toluene diisocyanates which are the monomers again depending on the temperature.

When the toluene diisocyanate unit alone is present, an amount of the dimer generated is gradually increased at a temperature of about 40° C. or more, and a generation rate is increased as the temperature is increased to 50° C. According to this tendency, when the temperature is 100° C. or more, a reverse reaction proceeds, and as the temperature increases, a decomposition rate from the dimer to the unit is also increased. As time passes, a forward reaction and the reverse reaction form an equilibrium state, and as the temperature is higher, the time to equilibrium is shortened.

By taking advantage of this tendency, the present invention provides a method of reducing the amount of toluene diisocyanate dimer generated.

Hereinafter, constitution of the present invention will be described in more detail with reference to the drawings.

Figure 2:
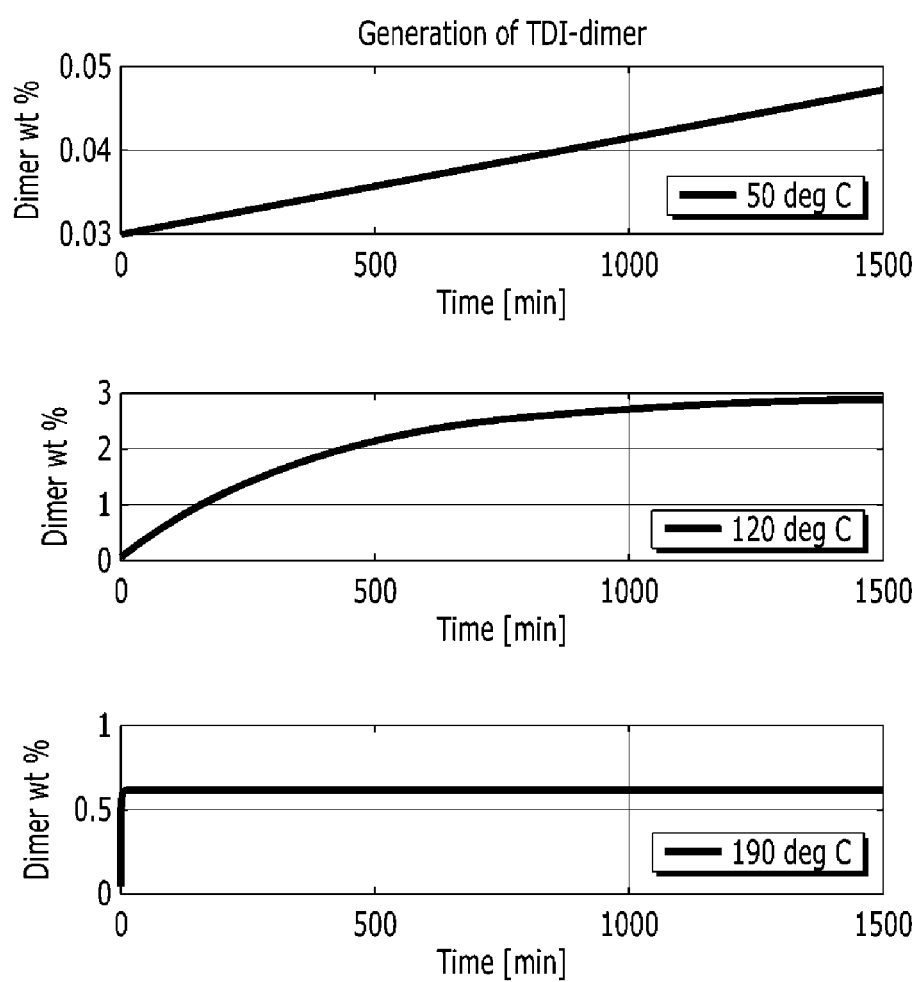
FIG. 2 shows comparison of generation contents of a toluene diisocyanate dimer by a reversible reaction according to a retention time at a low temperature and a high temperature (50° C., 120° C., and 190° C.).

FIG. 2 shows comparison of generation contents of the toluene diisocyanate dimer by a reversible reaction according to a retention time at a low temperature and a high temperature (50° C., 120° C., and 190° C.).

Accordingly, the present invention deals with a method of fractionating the low-boiling component and the high-boiling component while simultaneously obtaining a product in which dimers are contained in a remarkably small amount, in purification of toluene diisocyanate.

Preferably, the present inventors developed purification conditions in which the dimerization reaction was inhibited, which were obtained by calculating a dimerization reaction scheme by the reversible reaction according to the retention time at 50° C., 120° C., and 190° C. and reflecting this scheme to the column, as shown in FIG. 2.

Therefore, in the present invention, when toluene diisocyanate is finally purified with high purity after the solvent and the unreacted materials are recovered in advance from the reaction mixture obtained in the preparation of toluene diisocyanate, a reactive dividing wall column is used to remove the low-boiling components and the high-boiling components.

In addition, a pressure of the condenser is preferably maintained at 50 torr or less, preferably 15 torr or less, and more preferably 9 to 12 torr in operation. When the pressure of the condenser exceeds 50 torr, there is a problem in that the formation of the dimer is accelerated since an equilibrium temperature in the condenser is excessively high. When the pressure thereof is excessively low, there are problems in that an apparatus size is increased in order to adjust the hydraulics in the column, and the operation cost of the condenser is increased.

Further, the temperature of the condenser is maintained at 130° C. or less, preferably 70° C. or less, and more preferably 10 to 50° C., including supercooling. When the temperature of the condenser exceeds 130° C., there is a problem in that an initial amount of the dimer generated is increased. When the temperature is excessively low, there is a problem in that the operation cost of the condenser is increased.

In addition, the distillation apparatus is a reactive dividing wall column. The total pressure difference (pressure difference) in the reactive dividing wall column is 40 torr or less, preferably 15 torr or less, and more preferably 9 to 12 torr. When the total pressure difference in the column exceeds 40 torr, there is a problem in that temperature deviation in the column becomes large. When the pressure difference in the column is excessively low, there is a problem in that the apparatus size is increased in order to adjust the low pressure difference, or the cost of packing materials in the column is increased.

The retention time of the reaction mixture in the reactive dividing wall column may vary according to the temperature profile in the column. It is preferable to lower the equilibrium temperature accordingly by lowering the pressure as much as possible for the desired retention time. However, when the pressure is excessively low, the operating cost is increased, and an amount of boiling steam is increased in the reboiler. Therefore, a diameter of the entire column should be increased to meet a vapor-liquid equilibrium and prevent flooding. Therefore, it is very important to maintain the retention time of the reaction mixture in the column.

Accordingly, by adjusting the pressure and temperature conditions as described above, an appropriate retention time of the reaction mixture may be derived. Specifically, according to the present invention, the retention time of the reaction mixture in the reactive dividing wall column is maintained within 10 seconds to 150 seconds. More preferably, the retention time of the reaction mixture in the reactive dividing wall column is maintained between 10 seconds and 60 seconds. When the retention time exceeds 150 seconds, there is a problem in that the temperature in the column should be significantly lowered. When the retention time is less than 10 seconds, there is a problem in that the equipment investment cost is increased.

In addition, in the present invention, it is preferable to use a structured filler having a low pressure difference in order to lower the retention time of the reaction mixture in the column while simultaneously lowering the temperature deviation. This filler is made of plastic or metal, and may be at least one selected from the group consisting of structured fillers such as GRID, MELLAPAK, GEMPAK, and the like.

Further, in the present invention, the dimerization reaction is inhibited and formation of high-boiling impurities is inhibited by using a heat exchanger having a short retention time of the reaction mixture and a large heat transfer rate as a reboiler.

The retention time of the reaction mixture in the reboiler may be maintained within 3 minutes or within 3 minutes to 1 minute depending on the reboiler temperature. When the retention time of the reaction mixture in the reboiler becomes increased, a contact time with a high-temperature portion becomes increased, and thus a large amount of the high-boiling material such as tar, or the like, is generated, and the yield of the product is decreased.

Here, the pressure of the reboiler is preferably maintained at 30 torr or less, and preferably 18 to 21 torr, and the temperature of the reboiler is preferably maintained at 160° C. or less, and preferably 130 to 150° C. When the pressure of the reboiler exceeds 30 torr, the equilibrium temperature in the reboiler is excessively high, and thus the temperature in the column is entirely increased, and as a result, there is a problem in that the formation of the dimer is accelerated. When the pressure of the reboiler is excessively low, there is a problem in that a diameter of the column becomes increased in order to adjust the hydraulics in the column. In addition, when the temperature of the reboiler exceeds 160° C., there is a problem in that the formation of the dimer is accelerated as a result of the increase in pressure, and when the temperature of the reboiler is excessively low, there is a problem in that the temperature and the pressure of the condenser should be lowered.

In connection with this, toluene diisocyanate purified with high purity is quenched immediately and then transferred to a storage tank in order to inhibit the dimerization reaction.

Thus, after separating and purifying toluene diisocyanate, the method may further include quenching the purified toluene diisocyanate using a quencher (product quencher) at a temperature of 40° C. or less. Here, a quenching temperature is preferably 40° C. or less, more preferably room temperature to 40° C., and the quenching is the most preferably performed at room temperature. When the quenching temperature is 40° C. or more, the dimerization reaction may proceed, and thus the purity and yield of the product may be decreased. In addition, the quencher is preferably connected to a side part of the reactive dividing wall column.

In the present invention, the product containing toluene diisocyanate of which the purification is completed includes a trace amount of toluene diisocyanate dimer in an amount of 2,000 ppm or less, and more preferably 1,000 ppm or less. Therefore, it may be confirmed that in the present invention, the dimerization reaction of the product is inhibited as compared with the conventional method. In addition, the amount of purified toluene diisocyanate effused through the reactive dividing wall column of the present invention to the side draw zone is preferably about 85 wt % or more, more preferably about 95 wt % or more in the mixture entering the feed zone.

Meanwhile, FIG. 1 shows the reactive dividing wall column according to an embodiment of the present invention.

The present invention provides a method of purifying a product after unreacted materials and a solvent are separated in advance in preparation of toluene diisocyanate. The method of the present invention is a method of purifying a final product using the reactive dividing wall column as shown in FIG. 1 according to an embodiment, which is a method of inhibiting generation of a dimer material to improve the purity of the final product by specifically controlling the temperature and pressure of the reactive dividing wall column and the retention time of the reaction mixture in the column.

To this end, in the present invention, toluene diisocyanate is prepared by a general method using phosgene and toluene diamine in a solvent such as toluene, monochlorobenzene, or the like, the unreacted materials and solvent are separated in advance, and then finally, toluene diisocyanate with high purity is purified by using the reactive dividing wall column.

Further, the reactive dividing wall column used in the present invention includes at least one condenser, a main column having a dividing wall, and at least one reboiler, wherein the main column includes a fractionation zone having a dividing wall that vertically divides the mixture containing toluene diisocyanate as a main component into a preliminary fractionation zone and a main fractionation zone; a top zone removing the low-boiling component; a feed zone feeding the mixture containing toluene diisocyanate as a main component; an side draw zone effusing the separated and purified toluene diisocyanate; and a bottom zone removing the high-boiling component.

For example, the reactive dividing wall column used in the present invention may be a sidedraw column including at least one condenser, a main column having a dividing wall, and at least one reboiler.

Specifically, as shown in FIG. 1, the reactive dividing wall column of the present invention includes a main column 100 having a dividing wall 10, a condenser 200, and a reboiler 300, wherein the main column 100 Is largely divided into a top zone 20, a bottom zone 30, a feed zone A, and an side draw zone B, respectively.

In addition, the main column 100 includes the fractionation zone 40 for fractional distillation of feedstock and the fractionation zone 40 includes a preliminary fractionation zone 40a and a main fractionation zone 40b which are vertically divided based on the dividing wall 10. Further, although not shown in the drawings, upper and lower portions of the preliminary fractionation zone 40a and the main fractionation zone 40b may include zones in which fractionation distillation results are transferred to the top zone and the bottom zone.

Further, when a mixture containing toluene diisocyanate as a main component enters the fractionation zone 40, the mixture is transferred through the preliminary fractionation zone 40a and the main fractionation zone 40b to the upper and lower portions of the fractionation zone 40, wherein the low-boiling components, the solvent, and the like, are transferred to a rectification zone 22, and the high-boiling components, a liquid product, and the like, are transferred to a stripping zone 32.

Then, the mixture containing the product as the main component from the stripping zone is transferred to the main fractionation zone, and then the product may be recovered to the side draw zone effusing B on the side of the main fractionation zone through a series of processes.

Further, in the top zone 20 included in the main column, impurities including low-boiling components are separated through the upper part of the fractionation zone 40. These impurities may include chlorine-containing impurities, which are directly or indirectly generated from a trace amount of solvent and phosgene. In addition, the top zone may include the rectification zone 22.

The bottom zone 30 is a zone for removing impurities containing the high-boiling components through the lower portion of the fractionation zone 40, and may include the stripping zone 32.

In addition, the feed zone (A) is a zone in which the mixture containing toluene diisocyanate as a main component enters, which allows the mixture to flow to the preliminary fractionation zone 40a of the main column.

Further, the side draw zone B may be a zone through which the purified product is effused, and the product may be recovered through one or more condensers. In the main column 100, the side draw zone may be positioned at an intermediate stage of the top zone 20 and the bottom zone 30.

The fractionation zone 40 may represent 20% to 80% of appropriate theoretical stage relative to total column stages of the main column 100 and may be appropriately adjusted to be used. Here, the theoretical stage in the fractionation zone may be the same as the theoretical stage of the preliminary fractionation zone and the main fractionation zone, or may be appropriately adjusted as necessary.

The condenser 200 is an apparatus that takes a heat of vaporization of a gaseous mixture and condenses the mixture.

The reboiler 300 is an apparatus that provides the heat of vaporization to a liquid mixture to vaporize the liquid mixture. The reboiler of the present invention enables inhibition of the dimerization reaction described above while simultaneously inhibiting generation of high-boiling impurities by using a reboiler having a short retention time and a high heat transfer rate while simultaneously using a product quencher to be described below. Preferably, the reboiler 300 may include a falling film evaporator, a forced circulation evaporator, a pool boiling (kettle) evaporator, a natural circulation evaporator, a thin film evaporator, and the like. More preferably, the reboiler uses the falling film evaporator. In addition, when the reboiler of the present invention is used, the retention time at a high temperature contact part may be within 3 minutes, and preferably 1 minute to 2 minutes, as described above. In addition, when the falling film evaporator is used, a receiver may be added as needed in order to separate the vapor-liquid to be discharged. The quencher 400 is a quenching apparatus for preventing the reversible reaction after purifying the main component effused from the side draw zone to 90° C. or less, and may mean a product quencher. The product quencher may be a side product quencher positioned on the side of the column. When the product quencher is connected to a part other than the side of the column, amounts of the low-boiling impurities or the high-boiling impurities are increased, thus causing a problem in that the purity of the product is decreased. In addition, the product quencher may be a heat exchanger. Here, as a temperature of the quencher is lower, a size of the apparatus for heat exchange is increased. Thus, in this case, one or more quenchers may be constituted in series or in parallel.

The condenser 200 or quencher 400 may include cocurrent and countercurrent (knock-back condenser).

Further, the condenser and the reboiler are equipped with temperature and pressure regulating means.

The length of the dividing wall provided inside the main column may vary depending on the total stages of an upper part feed zone and a lower part supply zone.

For example, the length of the dividing wall may range from 20 to 80%, preferably from 30 to 80%, and more preferably from 40 to 80% of the total column stages of the main column. When the length of the dividing wall is less than 20%, a portion of the low-boiling component may fall down in the preliminary fractionation zone and may be included as a product of the main separator, and when the length thereof is more than 80%, it may be difficult to maintain a smooth equilibrium flow of a liquid phase/a vapor phase of the low-boiling component/middle-boiling component and a liquid phase/a vapor phase of the middle-boiling component/high-boiling component inside the column, thus causing a problem in manufacturing the column.

A temperature of the top zone of the main column may range from about 40 to 60° C. under a pressure of 12 to 15 torr. A temperature of the bottom zone of the main column may range from 140 to 160° C. under a pressure of 25 to 35 torr.

In addition, a temperature of the preliminary fractionation zone in the fractionation zone of the main column may range from about 125 to 150° C. under a pressure of 15 to 30 torr. A temperature of the main fractionation zone in the fractionation zone of the main column may range from about 125 to 150° C. under a pressure of 15 to 30 torr.

Meanwhile, a method of removing unreacted materials and solvent in order to obtain a subject to be purified after preparation of toluene diisocyanate may be performed by fractional distillation, multi-stage distillation, or using a dryer, and the like. The mixture obtained after the unreacted material and the solvent are separated from the reaction mixture by the above-described method contains toluene diisocyanate as a main component and includes the low-boiling components and the high-boiling components that are not recovered in the above-described process. For example, the mixture containing toluene diisocyanate as a main component may include 92 to 96 wt % of toluene diisocyanate, 0.01 to 1 wt % of the toluene diisocyanate dimer, 0.1 to 2 wt % of the low-boiling component, and 2 to 10 wt % of the high-boiling component, based on a total weight of the entire mixture.

Hereinafter, the present invention is described in more detail with reference to Examples according to the present invention. However, these Examples are merely illustrative of the invention and are not intended to limit the scope of the invention.

Example 1

In order to purify high-purity toluene diisocyanate including inhibition of the dimerization reaction, the feed was applied to the reactive dividing wall column shown in FIG. 1. Here, the feed had a composition including 1800 ppm of low-boiling component, 7 wt % of high-boiling component, 200 ppm of toluene diisocyanate dimer, and 92.8 wt % of toluene diisocyanate. In addition, the theoretical stage of the reactive dividing wall column was set to 30 stages in total.

Example 1 was performed by reducing the pressure and temperature of the condenser, reducing the pressure drop in the reactive dividing wall column, and also reducing the retention time according to conditions shown in Table 1 below.

TABLE 1

| Operating condition | Unit | Value |
|---|---|---|
| Condenser pressure | torr | 15 |
| Condenser temperature | ° C. | 54.5 |
| Reaction mixture retention time in column | sec. | 46 |
| Reboiler pressure Falling film evaporator | torr | 30 |
| Reboiler temperature | ° C. | 157.0 |
| Retention time in reboiler | sec. | 12 |
| Pressure drop in column | torr | 15 |

TABLE 1-continued

| Operating condition | Unit | Value |
|---|---|---|
| Product quencher Quenching temperature | ° C. | 40 |
| Dimer amount in product | ppm | 444 |
| High-boiling component amount | wt % | 7 |

From results of Table 1, it could be appreciated that the dimerization reaction could be inhibited at the time of purification of the product to reduce a dimer amount in the product as compared to the conventional case by appropriately specifying the condenser, the reboiler, the retention time, and the pressure drop conditions of the column.

Example 2

Example 2 was performed in the same manner as in Example 1 except that after toluene diisocyanate was separated and purified, when the purified toluene diisocyanate was quenched by using a side product quencher, a quenching temperature was 25° C.

TABLE 2

| Operating condition | Unit | Value |
|---|---|---|
| Condenser pressure | torr | 15 |
| Condenser temperature | ° C. | 54.5 |
| Reaction mixture retention time in column | sec. | 46 |
| Reboiler pressure Falling film evaporator | torr | 30 |
| Reboiler temperature | ° C. | 157.0 |
| Retention time in reboiler | sec. | 12 |
| Pressure drop in column | torr | 15 |
| Product quencher Quenching temperature | ° C. | 25 |
| Dimer amount in product | ppm | 442 |
| High-boiling component amount | wt % | 7 |

From results of Table 2, it could be appreciated that the dimer in the product could be reduced as compared to the conventional case by controlling the temperature to 40° C. or less during the quenching of the purified toluene diisocyanate.

Reference Example 1

Reference Example 1 was performed in the same manner as in Example 1 except that the retention time in the reboiler was changed as shown in Table 3.

TABLE 3

| Operating condition | Unit | Value |
|---|---|---|
| Condenser pressure | torr | 15 |
| Condenser temperature | ° C. | 54.5 |
| Reaction mixture retention time in column | sec. | 46 |
| Reboiler pressure Falling film evaporator | torr | 30 |
| Reboiler temperature | ° C. | 157.0 |
| Retention time in reboiler | sec. | 300 |
| Pressure drop in column | torr | 15 |
| Product quencher Quenching temperature | ° C. | 40 |
| Dimer amount in product | ppm | 444 |
| High-boiling component amount | wt % | 7.2 |

From results of Table 3, in Reference Example 1, the dimer amount in the product could be reduced as in Examples 1 and 2, but an amount of high-boiling component was increased.

Comparative Example 1

Comparative Example 1 was performed by increasing the pressure and temperature of the condenser and increasing the pressure drop in the column while the retention time was the same as that of Example 1 as shown in the conditions of Table 4 below.

TABLE 4

| Operating condition | Unit | Value |
| --- | --- | --- |
| Condenser pressure | torr | 75 |
| Condenser temperature | ° C. | 99.0 |
| Retention time | sec. | 46 |
| Reboiler pressure | torr | 120 |
| Reboiler temperature | ° C. | 197.1 |
| Pressure drop in column | torr | 45 |
| Dimer amount in product | ppm | 3788 |

From results of Table 4, it could be appreciated that in Comparative Example 1, the pressure and temperature of the condenser were high and the pressure drop in the column was excessively high, and thus the dimer in the product was excessively produced at 3788 ppm.

Comparative Example 2

Comparative Example 2 was performed by increasing the retention time in the column while the pressure and temperature of the condenser and the pressure drop in the column were the same as those of Example 1 as shown in the conditions of Table 5 below.

TABLE 5

| Operating condition | Unit | Value |
| --- | --- | --- |
| Condenser pressure | torr | 15 |
| Condenser temperature | ° C. | 54.5 |
| Retention time | sec. | 1021 |
| Reboiler pressure | torr | 30 |
| Reboiler temperature | ° C. | 160.1 |
| Pressure drop in column | torr | 15 |
| Dimer amount in product | ppm | 3947 |

From results of Table 5, it could be appreciated that in Comparative Example 2, as the retention time in the column was increased, the dimer in the product was excessively produced at 3947 ppm.

Reference Example 2

Reference Example 2 was performed in the same manner as in Example 1 except that after toluene diisocyanate was separated and purified, the purified toluene diisocyanate was quenched to 75° C. using a side product quencher.

TABLE 6

| Operating condition | Unit | Value |
| --- | --- | --- |
| Condenser pressure | torr | 15 |
| Condenser temperature | ° C. | 54.5 |
| Reaction mixture retention time in column | sec. | 46 |
| Reboiler pressure | torr | 30 |
| Falling film evaporator Reboiler temperature | ° C. | 157.0 |
| Retention time in reboiler | sec. | 12 |
| Pressure drop in column | torr | 15 |
| Product quencher Quenching temperature | ° C. | 75 |
| Dimer amount in product | ppm | 537 |

From results of Table 6, when a quenching temperature was set to 40° C. or more, the dimer amount in the product was smaller than those of Comparative Examples 1 to 2, but the dimer amount was larger than that of Example 1 of the present invention.

Therefore, when toluene diisocyanate is purified, it is important to control conditions of the condenser. Further, a small amount of dimer may be included in the final product by appropriately adjusting conditions for the reactive dividing wall column, quenching conditions, conditions for the reboiler, and the like, within the scope of the present invention.

DESCRIPTION OF SYMBOLS

10: Dividing wall
20: Top zone
22: Rectification zone
30: Bottom zone
32: Stripping zone
40: Fractionation zone
40a: Preliminary fractionation zone
40b: Main fractionation zone
A: Feed zone
B: Side draw zone
100: Main column
200: Condenser
300: Reboiler
400: Quencher

The invention claimed is:
1. A toluene diisocyanate purification method comprising:
separating and purifying toluene diisocyanate by feeding a mixture containing toluene diisocyanate as a main component to a reactive dividing wall column equipped with a condenser and a reboiler,
wherein a pressure of the condenser is maintained at 50 torr or less, and a temperature of the condenser is maintained at 130° C. or less,
a total pressure difference in the reactive dividing wall column is maintained at 40 torr or less,
a retention time of the reaction mixture in the reactive dividing wall column is maintained within 10 seconds to 150 seconds, and
a pressure of the reboiler is maintained at 30 torr or less, and a temperature of the reboiler is maintained at 160° C. or less.
2. The toluene diisocyanate purification method of claim 1, wherein:
the mixture containing toluene diisocyanate as a main component includes toluene diisocyanate, a toluene diisocyanate dimer, a low-boiling component, and a high-boiling component, and
the mixture containing toluene diisocyanate as a main component is obtained by separating unreacted mate- rials and a solvent from a mixture in which phosgene and toluenediamine are reacted in the solvent.

3. The toluene diisocyanate purification method of claim 2, wherein: the mixture containing toluene diisocyanate as a main component includes 92 to 96 wt % of toluene diisocyanate, 0.01 to 1 wt % of the toluene diisocyanate dimer, 0.1 to 2 wt % of the low-boiling component, and 2 to 10 wt % of the high-boiling component, based on a total weight of the entire mixture.

4. The toluene diisocyanate purification method of claim 1, wherein:

the condenser is maintained at a pressure of 9 to 50 torr and a temperature of 10 to 130° C.

5. The toluene diisocyanate purification method of claim 1, wherein:

the total pressure difference in the reactive dividing wall column is maintained at 9 to 40 torr.

6. The toluene diisocyanate purification method of claim 1, wherein:

the retention time of the reaction mixture in the reactive dividing wall column is maintained within 10 seconds to 60 seconds.

7. The toluene diisocyanate purification method of claim 1, wherein:

a retention time in the reboiler is maintained within 1 minute to 3 minutes.

8. The toluene diisocyanate purification method of claim 1, further comprising:

after the separating and purifying of toluene diisocyanate, quenching the purified toluene diisocyanate using a quencher at a temperature of 40° C. or less.

9. The toluene diisocyanate purification method of claim 8, wherein:

the quencher is connected to a side part of the reactive dividing wall column.

10. The toluene diisocyanate purification method of claim 1, wherein:

the separated and purified toluene diisocyanate product comprises 2000 ppm or less of a toluene diisocyanate dimer.

11. The toluene diisocyanate purification method of claim 1, wherein: the reactive dividing wall column includes at least one condenser, a main column having a dividing wall, and at least one reboiler, and the main column includes a fractionation zone having a dividing wall that vertically divides the mixture containing toluene diisocyanate as a main component including toluene diisocyanate, a toluene diisocyanate dimer, a low-boiling component, and a high-boiling component into a preliminary fractionation zone and a main fractionation zone;

a top zone for removing the low-boiling component;

a feed zone for feeding the mixture containing toluene diisocyanate as a main component;

a side draw zone for effusing the separated and purified toluene diisocyanate; and a bottom zone for removing the high-boiling component.

12. The toluene diisocyanate purification method of claim 11, wherein:

the side draw zone is positioned at an intermediate stage between the top zone and the bottom zone.

13. The toluene diisocyanate purification method of claim 11, wherein:

the fractionation zone represents 20% to 80% of the theoretical stages relative to total column stages of the main column.

\* \* \* \* \*